(12) United States Patent
Aidun et al.

(10) Patent No.: US 7,745,204 B1
(45) Date of Patent: Jun. 29, 2010

(54) AUTOMATION OF BIOLOGICAL SAMPLE ALIQUOTING

(75) Inventors: Cyrus K. Aidun, Marietta, GA (US); Amanda C. Sozer, Fairfax Station, VA (US)

(73) Assignee: Georgia Tech Research Corporation, Atlanta, GA (US)

( * ) Notice: Subject to any disclaimer, the term of this patent is extended or adjusted under 35 U.S.C. 154(b) by 859 days.

(21) Appl. No.: 11/380,239

(22) Filed: Apr. 26, 2006

Related U.S. Application Data

(60) Provisional application No. 60/676,612, filed on Apr. 29, 2005.

(51) Int. Cl.
*C12M 1/36* (2006.01)
*C12M 1/26* (2006.01)

(52) U.S. Cl. .................. 435/286.2; 435/287.3; 422/63; 422/65; 83/167

(58) Field of Classification Search .............. 435/286.2, 435/287.3; 422/63, 65; 83/167
See application file for complete search history.

(56) References Cited

U.S. PATENT DOCUMENTS

| | | | |
|---|---|---|---|
| 2,397,417 A | 3/1946 | Holaday | |
| 3,698,040 A | 10/1972 | Mourkakos | |
| 3,835,834 A | 9/1974 | Brown et al. | |
| 4,398,327 A | 8/1983 | Yamazaki | |
| 4,523,366 A | 6/1985 | Lodge et al. | |
| 4,753,349 A | 6/1988 | Monek | |
| 4,777,964 A | 10/1988 | Briggs et al. | |
| 4,862,899 A | 9/1989 | Bucaro | |
| 4,903,708 A | 2/1990 | Saint-Amand | |
| 5,266,266 A | 11/1993 | Nason | |
| 5,358,690 A | 10/1994 | Guirguis | |
| 5,547,872 A | 8/1996 | Schalkowsky et al. | |
| 5,616,499 A | 4/1997 | Eckner et al. | |
| 5,638,170 A * | 6/1997 | Trinka et al. ................. | 356/244 |
| 5,965,453 A | 10/1999 | Skiffington et al. | |
| 6,036,658 A | 3/2000 | Leet et al. | |
| 6,312,395 B1 | 11/2001 | Tripp et al. | |
| 7,063,216 B2 * | 6/2006 | Lane et al. ................... | 210/466 |
| 2002/0110812 A1 | 8/2002 | Naegele | |
| 2004/0014228 A1* | 1/2004 | Brignac et al. ................. | 436/43 |
| 2004/0161788 A1 | 8/2004 | Chen et al. | |
| 2004/0267562 A1 | 12/2004 | Fuhrer et al. | |
| 2005/0026279 A1 | 2/2005 | Tseng et al. | |
| 2005/0032097 A1 | 2/2005 | Garvin | |

FOREIGN PATENT DOCUMENTS

| | | |
|---|---|---|
| EP | 0 371 574 A1 | 6/1990 |
| EP | 0 484 579 A1 | 5/1992 |
| EP | 1 510 578 A2 | 2/2005 |
| WO | WO94/22580 A1 | 10/1994 |
| WO | WO2004003515 A2 | 1/2004 |

* cited by examiner

*Primary Examiner*—William H Beisner
(74) *Attorney, Agent, or Firm*—Thomas, Kayden, Horstemeyer & Risley, LLP

(57) ABSTRACT

An automated biological sample aliquoting processing system is disclosed for handling biological samples. The system reads and records a sample identification number, cuts a biological sample, and places a portion of the biological sample into a specific location in a multi-well plate. The system ensures sample integrity and also greatly reduces the man hours currently required to process biological samples. The system, which automates sample cutting and aliquoting, reduces the time and cost of operation, while eliminating manual steps in a laboratory process.

15 Claims, 19 Drawing Sheets

Plate Set-up
Plate #

Enter Plate #
Scan from plate (will typically coincide with 4bII or III)
→ Scan from Plate
→ Please scan or hand enter plate #
[scan plate & put on machine]

Obtain from worklist (will typically coincide with 4bI)
→ Obtain from worksheet
→ Go to file list of batches ready to be processed → move to Plate
[produced by Lims. Plate #, # of samples, list of samples]

FIG. 5

Identify Controls
(Controls will be identified based on plate map)

Position        Positive Control        Position        Negative Control

G1 (generated from template)                            G12

D3

B11

[Back]   [Clear]   [Comment]

Name

After all (+ or −) Controls are Entered

Are these controls correct?

√ Yes → Identify-go to samples page (4b)

√ No → Back to blank page of identify controls

FIG. 7

Reports

☐ Print Comments/Pictures    enter or elect plate

☐ Export Comments/Pictures    enter or select plate

☐ Print log file

☐ Export log file

☐ Print pending plates

☐ Export error repots not previously exported

Reports printed or exported electronically

FIG. 11

Edit Default Parameters

Plate set-up:
  ☐ Scan from plate
  ☐ Obtain from worklist

Map Plate:
  ☐ Use defined template
  ☐ Generate new template

Identify Samples:
  ☐ I. Predetermined list | Populate plate | Order of placement
  ☐ horizontally | ☐ Numerical
  ☐ vertically | ☐ As listed ☐ II. By scanning | Populate plate
  ☐ | ☐ horizontally ☐ vertically ☐ III. As introduced into cutting mechanism Verify sample position prior to cutting:
  ☐ Yes (if yes, verification step will appear on (6) sample processing)
  ☐ No # of control placements to avoid:
  ☐ Number can be 0 - 96

FIG. 12

Map – Plate

Template Number _____

[Accept] [Reject]

☐ Yes ☐ No

If template number already exists, ask for a different number. If not, confirm and if confirmed then accept and add to the template list in the previous page, and write:

"Template # successfully created and added to the template list"

[OK]

Contents of Plate: 96 well

- Nothing –
    - Specified by user – template

- Extraction Positive Controls (known samples)
  (Typically 0-3 controls on a plate)
    - Specific location
        - Generated by software? (fingerprint plate)
      or
        - Or specified by user
            (user needs to input control #)

- Extraction Negative Control (blank, nothing on it)
    - Specified by user – template

- Samples
    - From predefined list – from # on software (verify)
  or
    - Introduced by user
  or
    - Introduced by user → placed in numerical order

FIG. 15

Required Information

- Plate Number (no duplicates, must be unique)
- Instrument User
- Date/time
- Samples on Plate
- Controls on Plate
- Comments (for each plate)
- Update LIMS

FIG. 16

Plate Map Features

Features:

- Color code samples and controls

- Fingerprint Plate

- Sort samples/arrange

- Errors –

– Print report
    – Send to LIMS

FIG. 17

Plate Set-up

Assign Plate #
- Auto – electronic (from LIMS)
- Main – keyboard (type in or scan)

Controls
- Template
- Computer driven
- Both

Samples
- Auto – electronic (from LIMS)
- Man – keyboard/scan

Update LIMS

FIG. 18

AUTOMATION OF BIOLOGICAL SAMPLE ALIQUOTING

CROSS REFERENCE TO RELATED APPLICATIONS

This application claims priority to U.S. Provisional Patent Application entitled "Automation of Buccal Swab Processing System" filed on Apr. 29, 2005 and assigned Application No. 60/676,612, the entire text and drawings of which are incorporated herein by reference.

TECHNICAL FIELD

The present disclosure generally relates to processing biological samples. More particularly, systems and methods for the automation of biological swab processing are disclosed.

BACKGROUND

Aliquoting is one of the first steps in biological sample processing whereby the sample or a portion of the samples is taken from the collection device and placed in an appropriate testing container for further processing. The testing of buccal cells on cotton-tipped or Dacron applicators in large scale DNA profiling from known individuals or forensic evidence is desirable because the collection of the sample is relatively easy, collection materials are inexpensive, and if collected properly, the cells on the swab yield a sufficient quantity of DNA. Unfortunately, unlike the processing of paper based collection substrates, there are in general no automated methods for introducing the buccal sample on the applicator into the laboratory testing process. Currently, sample introduction or aliquoting practices require the forensic analysis to manually cut or transfer each swab and place it into the correct well in a sample plate or tube. This process is labor intensive, typically requires a witness, and if not performed properly, can lead to the occurrence of sample switches or misidentifications.

Further, other contact methods, such as a mechanical shear technique, are used to cut biological samples on paper. The mechanical shear technique is based on cutting the sample with such devices as a punching unit, a razor blade, or scissors. Mechanical shear techniques are relatively simple but are also inflexible. Since these methods involve direct contact with the sample, there is also an increased chance of sample-to-sample contamination during the cutting operation. For situations where contamination or carryover is an issue, the cutting device may need to be cleaned or replaced between the cutting of samples, which can be expensive and time consuming. Also, contact methods can introduce static electricity which can sometimes lead to the sample "jumping." This inadvertent movement can lead to sample mix-up and misidentification. Currently there are no automated methods for cutting three-dimensional sample collection devices such as swabs, sponges, or three-dimensional paper devices.

SUMMARY

In response to these and other shortcomings of the prior art, an automated non-contact method for introducing a biological sample into the laboratory testing process is needed. A robotic instrument which reads and records the sample identification number, cuts the biological swab and places it into a specific location in a tube or multi-well plate ensures sample integrity and also greatly reduces the man hours currently required to process biological swab samples. The automation of sample cutting and aliquoting reduces the time and cost of operation while eliminating a manual step in a laboratory process.

Other systems, methods, features, and advantages of the present disclosure will be or become apparent to one with skill in the art upon examination of the following drawings and detailed description. It is intended that such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 5 is a diagram depicting the plate set-up functionality according to an embodiment of the present invention;

FIG. 7 is a diagram depicting the identify controls according to an embodiment of the present invention;

FIG. 11 is a diagram depicting reports functionality according to an embodiment of the present invention;

FIG. 12 is a diagram depicting edit default parameters functionality according to an embodiment of the present invention;

FIG. 15 shows the contents of a 96 well plate according to an embodiment of the present invention;

FIG. 16 shows the required information according to an embodiment of the present invention;

FIG. 17 shows the plate map features according to an embodiment of the present invention; and FIG. 18 shows the plate set-up steps according to an embodiment of the present invention.

DETAILED DESCRIPTION

Figure 1:
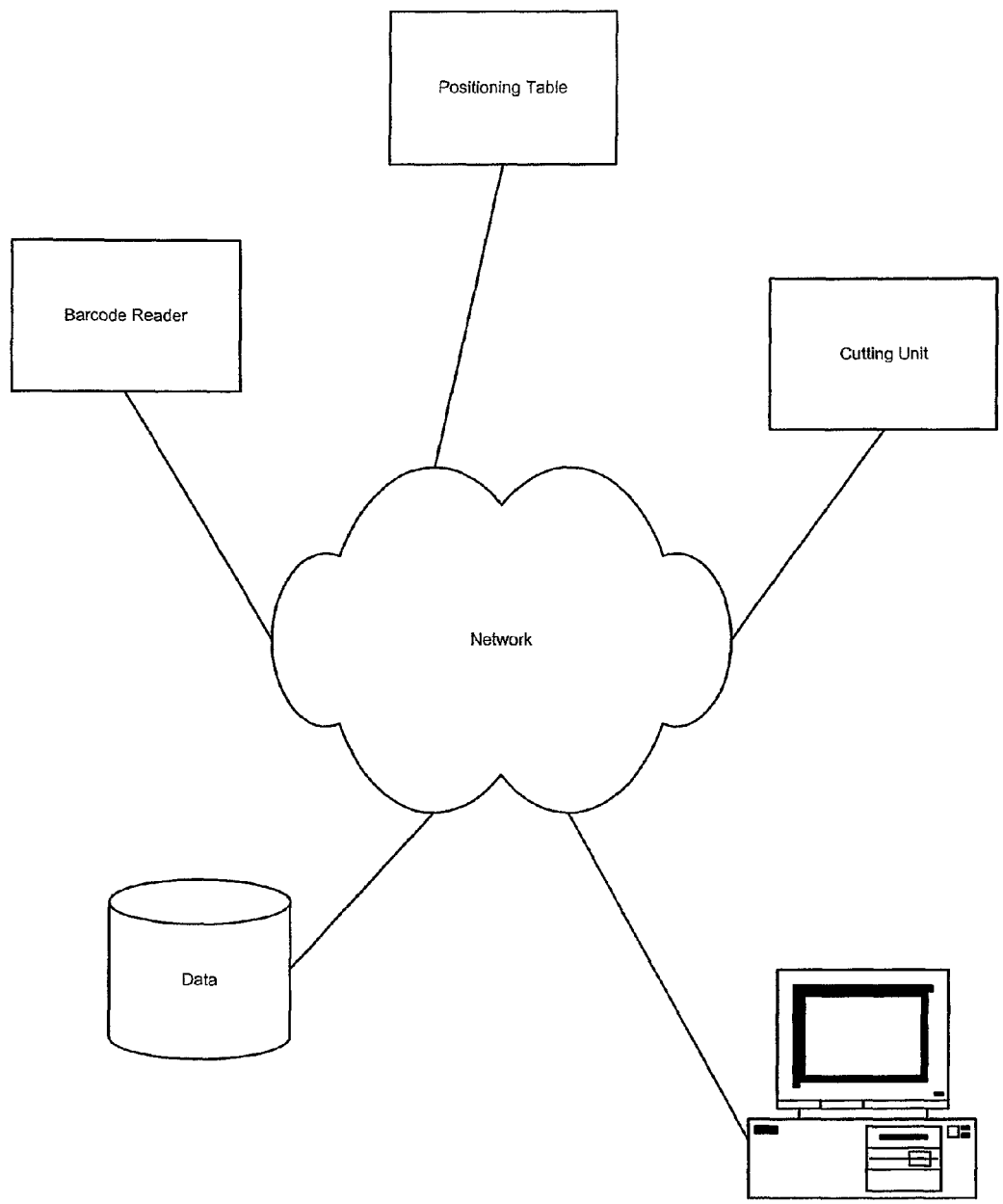
FIGS. 1 and 1A are exemplary system diagrams of the biological sample aliquoting system according to an embodiment of the present invention.

Various aspects of the system and method for the automation of biological sample aliquoting processing, having been summarized above, reference is now made in detail to the description of the embodiments as illustrated in the drawings.

The disclosure may, however, be embodied in many different forms and should not be construed as limited to the embodiments set forth herein; rather, these embodiments are intended to convey the scope of the disclosure to those skilled in the art. Furthermore, "examples" given herein are intended to be non-limiting.

The present disclosure provides systems and methods for the automation of biological sample aliquoting processing. Illustrated in the various figures is a system that can automatically transfer a piece of the biological sample into a designated location in a tube or multi-well plate in a reliable and accurate fashion. The plate can have any number of wells, but in the preferred embodiment, it has 96 wells with 12 columns and 8 rows. The samples are tracked with a consistent and reliable procedure coupled with the automated instrumentation to cut and place the sample in the designated location in the multi-well plate. The automation of sample cutting and aliquoting reduces the time and cost of operation, while eliminating manual steps in the laboratory process. No special preparation of the biological samples is necessary once the samples have been collected. Further, the system allows for the cutting of samples in a three-dimensional fashion and is not limited to having samples placed on paper or slides.

Biological collection devices are used for the collection of biological samples at a collection point usually outside of the testing laboratory. The collection device stores the sample which may then be transported from a collection location to a final destination, as necessary. For example, a collection device may be cotton swabs, Dacron swabs, or paper carriers in various forms (two-dimensional or three-dimensional), sponge, or other types of paper or cloth, among others. The collection of samples involves the acquisition of the biological material by touching to, rubbing over, or moving over, a biological sample with the collection material or placing a biological sample onto the collection material. Some or all of the biological material is moved from its original location to the collection material on the collection device. This collection device and material is then taken to the laboratory for potential testing, analysis, and storage.

While buccal swabs are the most common method of obtaining samples for DNA processing from known individuals, the automation of sample aliquoting may readily be applied to other types of testing and samples requiring aliquoting for possible analysis including blood samples, saliva samples, urine samples, feces samples, microbial samples, pathogens samples, forensic biological samples, crime scene biological samples, as well as samples related to security issues, terrorist attacks, microbial genetics, human genetics, forensic genetics, disease diagnostics, medical screening, identification, drug use, alcohol use, chemicals, and residues, among others. The automation of sample aliquoting is not limited to biological samples.

Figure 1A:
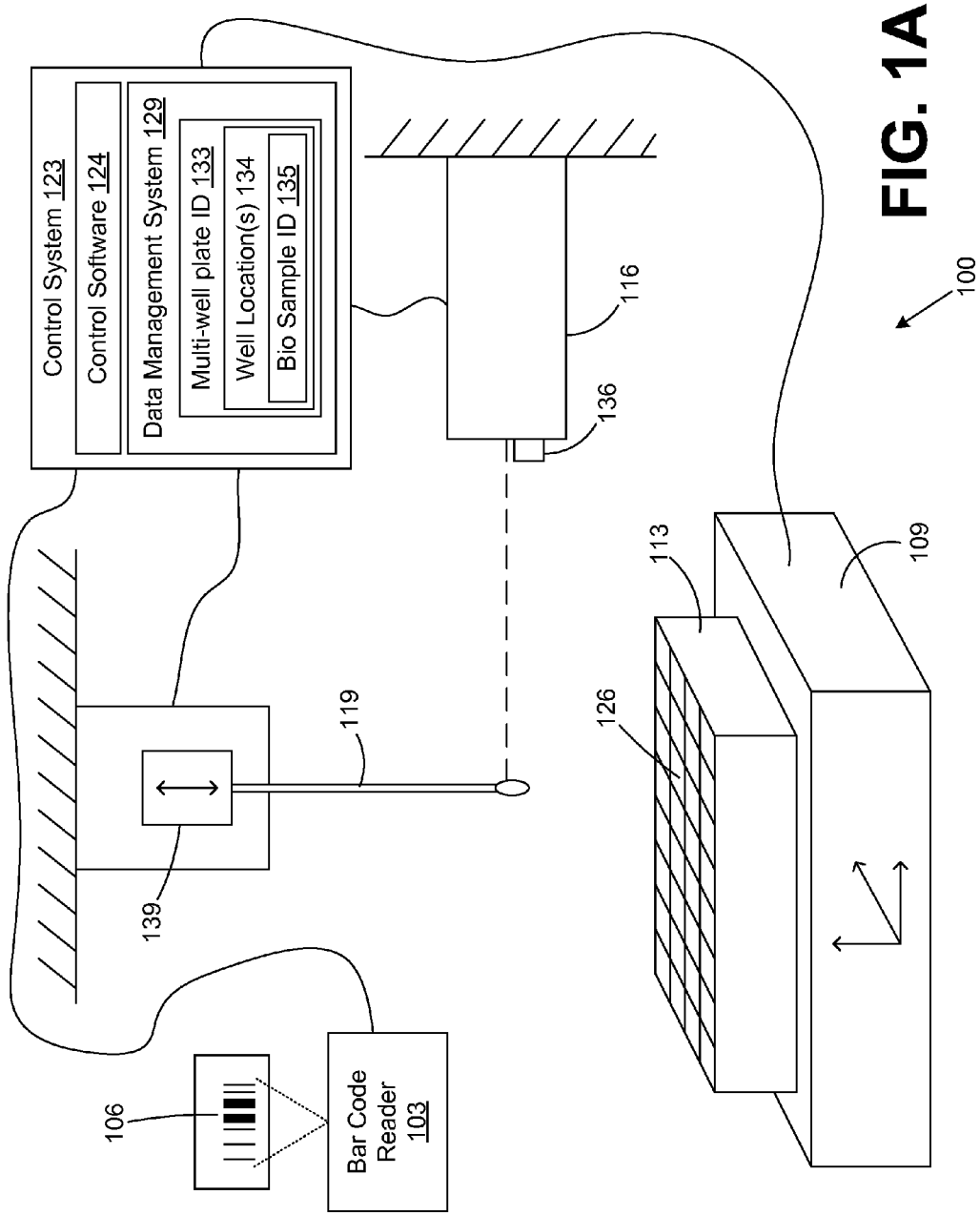

An embodiment of the system, as shown in FIG. 1, comprises a reader that can read a machine readable indicator (for example and preferably, but not limited to, a bar code reader), a computer controlled positioning table for the multi-well plate(s) or tube(s), a cutting unit, a data management system, and the control and integration software. The control and integration software may reside in one or more general purpose computers. The actual cutting can be by performed by non-contact cutting techniques as will be described below. With reference to FIG. 1A, according to one embodiment, shown is an automated biological sample processing system 100 comprising a reader 103 such as a bar code reader for reading a machine readable indicator 106, and a positioning table 109 for positioning a multi-well plate 113. Further shown is a cutting unit 116 for cutting a biological collection device 119 having a biological sample using a non-contact technique such as using a laser. A control system 123 comprises a general purpose computer with control software 124 for causing a part of the biological collection device 119 containing at least a part of the biological sample to be directed into a well 126 within the multi-well plate 113. A data management system 129 maintains identification number(s) 133 of one or more multi-well plates 113 and at least one biological sample identification number that corresponds to one of the at least one multi-well plate(s) and a well location 134 of at least one biological sample identification number 135 within the at least one multi-well plate(s) 113. Further shown is an optical sensor 136 for adjusting the height of the biological collection device 119 to an appropriate cut position. The automatic biological sample processing system 100 includes a sample loading system 139 for loading the biological collection device 119. The sample loading system 139 may comprise, for example, an automated robotic sample loading system, an automated pneumatic sample loading system, an automated magnetic sample loading system, or a manual sample loading system.

In the operating environment shown in FIG. 1, a user of a general purpose computer utilizes the control and integration software to control the system comprising a $CO_2$ laser cutting device, a high-precision two axis galvanometer, a computer controlled three axis X-Y-Z positioning table, a one axis translator, and a one axis translator with an optical sensor for sample loading and positioning. The system also provides features for well plate mapping, sample setup and processing, barcode reading and identification of the samples, data storage and interaction with existing data management systems. Finally, the system provides graphical menu-driven features for user interface. The control and integration software can be implemented in software, firmware, hardware, or a combination thereof. According to an exemplary embodiment, the control and integration software is implemented in software, as an executable program, and is executed by a special or general purpose digital computer, such as a personal computer, workstation, minicomputer, or mainframe computer.

It should also be noted that the system is conducive to various kinds of sample loading systems. A mechanical system may use a fully automated robotic sample loading system. An air driven system may use a fully automated pneumatic sample loading system. An automated magnetic sample loading system could also be implemented. The samples could even be loaded manually. Those skilled in the art will recognize that numerous methods exist for loading the samples into the system.

An exemplary embodiment of the system utilizes a Class I laser enclosure. As such, during normal operation, the laser beam is not accessible to human exposure. Further, the laser cutting system should preferably comply with the requirements of 21 C.F.R. Subchapter J. The laser cutter preferably comprises a 40 Watt $CO_2$ laser packaged in a laser enclosure bolted in a horizontal configuration. The sealed-tube, RF-excited, $CO_2$ laser generates a high-intensity beam of far-infrared light at the 10.6 micron wavelength. The sealed $CO_2$ lasers have long operating lifetimes and can provide 24-hour-a-day operation for many months with little or no maintenance requirements. Those of skill in the art will readily recognize that many other laser devices could implement the cutting functionality.

The electronics are contained inside the laser enclosure and contain the Main Disconnect, Servo Power Supplies, Servo Control Cards, the Control Relays, and the Laser Power Supply. There is one I/O rack used in the system. The main rack, in a PC enclosure, controls the signals for the laser system.

Further, an Operator Panel is located on the front rail of the laser enclosure. Switches are available to (1) provide a visual signal to the operator concerning the laser status and system operation, (2) provide for disabling laser power in an emergency, (3), apply power to the system, and (4) provide power for the Galvo/Servo Electronics and the laser.

The main controller in the system is a Windows XP processor that utilizes software to control the system. Appropriate cutting data is sent to a Cutting PC after the contact is in place and motion has occurred. Communication to the axes controllers are serial and communication to the Cutting PC is through a network connection. The Cutting PC also controls the X table. One of skill in the art will readily recognize that many combinations of digital computers and/or controllers may be used to control the system.

The interface of the laser cutting system provides Operator Panel controls. An emergency stop button is provided to disable the laser and galvo/servo power. After the emergency stop is activated the laser power would preferably be manually re-energized before continuing. A laser emission indicator is coupled to the front panel Key Switch, which also supplies power to the circuitry in the laser enclosure. The indicator does not signify laser emission, but rather shows that laser power supply is energized and capable of emission. The Shutter Open lamp indicates that the shutter is open, and that lasing is possible when lit. Continuing operations require activating the System Enable button to supply power to the laser.

The laser beam is directed across the targeted cutting surface by mirrors mounted on high-speed, high accuracy galvanometers controlled by the main controller or system computer. The part-cutting software instructs the galvanometers to move the beam in order to cut the sample. Preferably, a flat-field lens assembly focuses the laser beam on the target surface to achieve the desired cutting effect. The operator may establish the cutting parameters for each element of the cutting image.

In one embodiment, among others, a workstation may be assembled in a stand alone configuration with a modular frame supporting the laser head, electronics enclosure, operator's control panel, and safety enclosure. The enclosure may accommodate a 6"×6" X-Y positioning table with 1" of Z-axis integrated digital positioning capability. The system can also accommodate multiple multi-well plates if the sample is to be placed into more than one location at aliquoting. The operator's keyboard, monitor and workstation controls may be mounted next to a load/unload station. A control panel indicates the system status and also contains an emergency stop button. Other commands are preferably entered through the operator's keyboard. A control electronics cabinet houses the servo power supplies, control circuit power supply, I/O interface and main power disconnect. Electrical wiring is routed through a subpanel in the back of the enclosure and the power required by the system is distributed from this point.

Laser processing of many materials produces a "smoke" of vaporized particles. These particles are removed via fume evacuation through appropriate ducting in the enclosure to protect the beam delivery optics. A vacuum system removes particulate from the cutting area.

Another embodiment of the system, among others, comprises a bar code reader, a precision X-Y positioning table for the well plate, a cutting unit utilizing the non-contact technique, and the control and integration software. Non-intrusive techniques have the advantage of cutting the sample with a significantly reduced possibility of contamination. Two exemplary methods of non-contact cutting high-speed water jet cutting and laser cutting. High speed water jet cutting is routinely used for cutting materials, such as food products, where contamination is of concern and has the further advantage of not damaging any of the cells.

The laser technique is a non-contact technique that provides flexibility, speed and ease of operation. Laser cutting is routinely used for precision cutting of a broad range of materials including plastics and textile. The diameter of the laser beam is a fraction of a millimeter and therefore can be precise in cutting of material. The high intensity incident beam will cut the sample by rapid vaporization of the material in its path. The cells exposed to the laser beam may be destroyed. However, the heat from the laser beam remains only near the exposed area and therefore the cells on the remaining portion of the sample will not be affected. In this embodiment of the system, the laser cutting device is used to cut the cotton swab from the base. One of skill in the art will readily recognize that this method can be easily modified to cut sections from other sample collection devices such as, among others, sponges, any other kind of swabs, as well as papers, plastics, or polymers.

Figure 2:
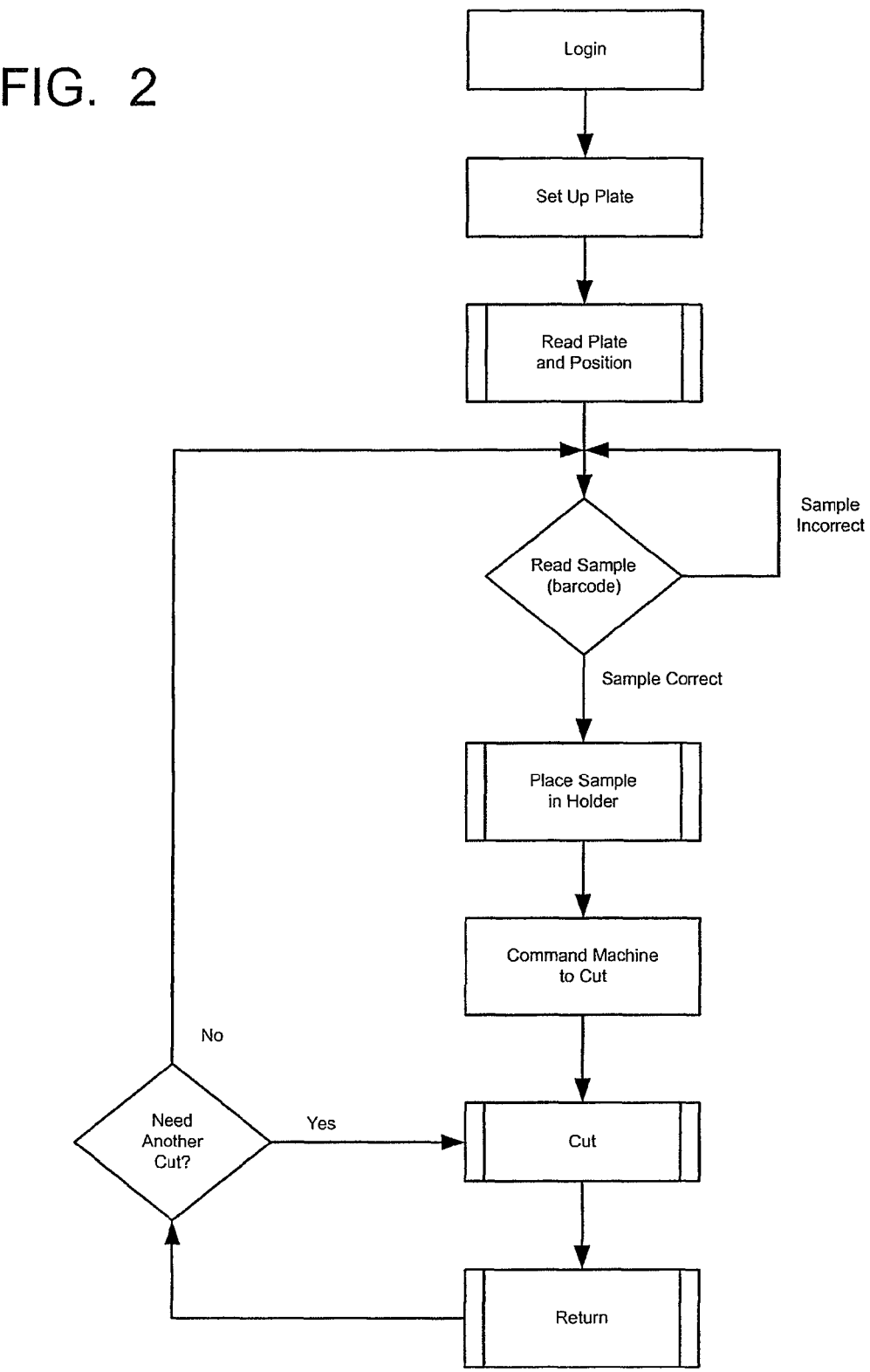
FIG. 2 is a flowchart depicting the process overview according to an embodiment of the present invention.

In one embodiment, among others, the system comprises a bar code reader, a computer controlled X-Y translator table, the cutting unit, and the system integration software. As illustrated via the flowchart in FIG. 2, the unit records the plate or tray identifier and prompts the user to define a plate map by indicating the number of samples to be tested and the location of the controls. Additional information can be incorporated to customize the procedure at the end-user's discretion. Once the plate map is created, the X-Y translator positions the first well under the sample cutter. The user then places the first sample in the sample holder and the system reads the bar code associated with the sample. Also, as a quality control check, the integration software may compare the sample identification number against a data base of samples previously designated by other software programs to be on the plate and any other specification(s) provided by the user. If the sample is to be tested, the cutting is be triggered. If there is a problem with the sample, then the operator is notified. Once the swab is cut, the sample is placed into the correct well or wells. The system verifies correct sample placement prior to the plate automatically moving to the designated location for introduction of the next sample.

In exemplary usage, an operator loads a desired swab-cutting program corresponding to the swab to be processed. The operator loads the swab onto the Z translator arm. The software causes the digitally controlled X-Y-Z positioning table to be positioned so that the well plate is in the appropriate position to receive the cut sample. The Z translator along with the optical sensor locates the tip of the cotton swab or the sample, and adjusts the height to the user pre-specified height for the appropriate cut position. The operator may then initiate the cutting cycle. The X translator positions the swab in the cutting field and cuts the swab to complete the cutting program. On completion, the system notifies the operator. The cutting operation takes less than 2 seconds and may be viewed on the monitor via live camera. The operators may remove the completed swab, insert a new swab, and repeat the process. One of skill in the art will appreciate that the swab loading process may be automated to include a cartridge with multiple swabs being automatically loaded and cut in the laser cutting unit.

Figure 3:
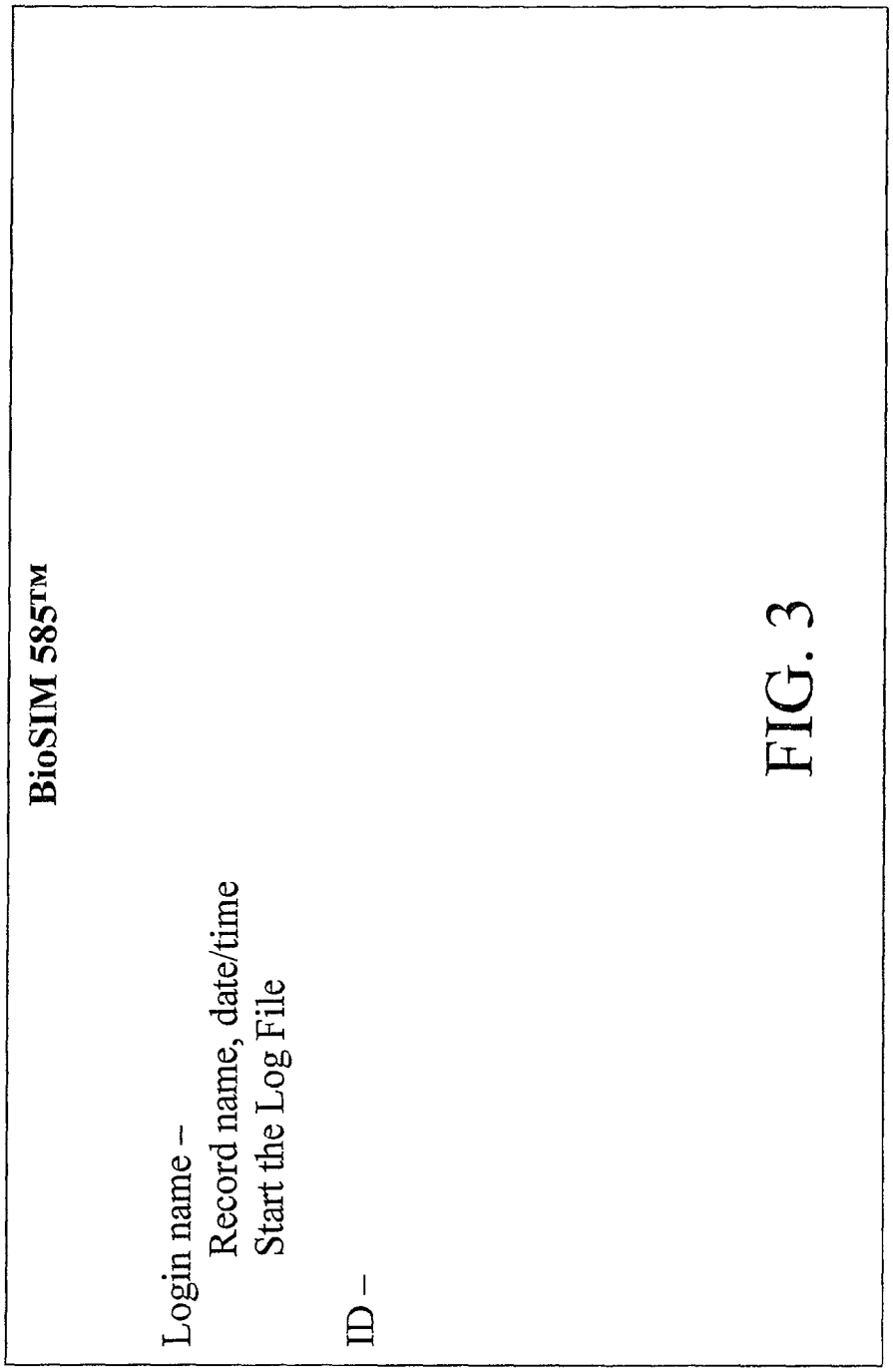
FIG. 3 is a diagram depicting name, date/time and log file information initiation according to an embodiment of the present invention.

The diagram in FIG. 3 illustrates that the system prompts the user for a login name. After the user responds with a login name, the login name is recorded along with the date and time. The system creates a log file for maintaining a systemwide log, and also maintains a plate specific log that includes tracking of the well plate identification (ID), sample ID, and well location.

Figure 4:
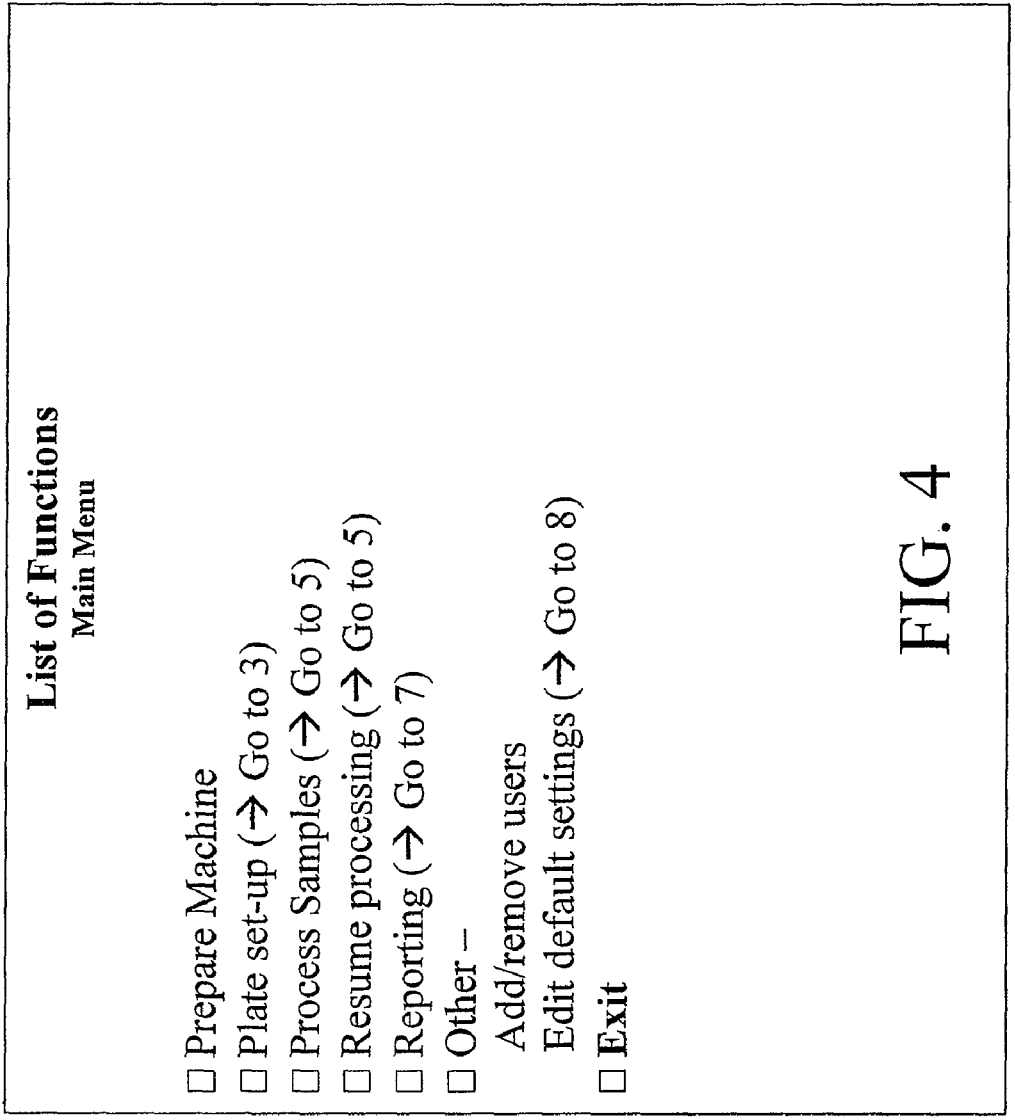
FIG. 4 is a diagram depicting the main menu according to an embodiment of the present invention.
Figure 9:
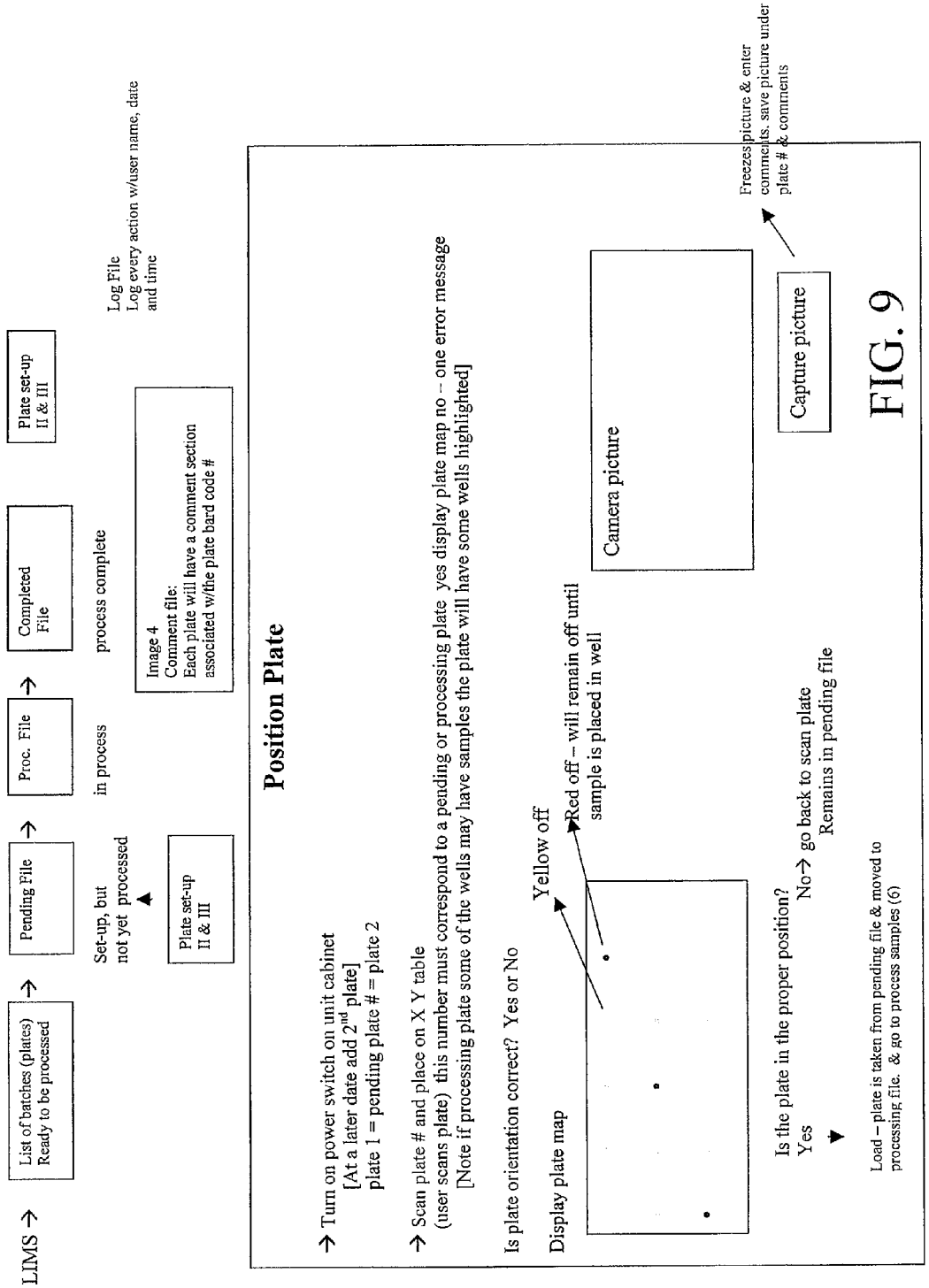
FIG. 9 is a diagram depicting the position plate functionality according to an embodiment of the present invention.

The diagram in FIG. 4 illustrates the list of functions that may be accessed from the main menu. The user may select options such as Prepare Machine, Plate set-up, Process Samples, Resume Processing, Reporting, Other, and Exit. Selecting the Prepare Machine option prepares the machine for operation. Selecting the Plate set-up option causes execution to proceed to the Plate set-up functionality shown in FIG. 5, and discussed below. The Process Samples option causes execution to proceed with the processing of biological samples as shown in FIG. 9, and discussed below. The Resume Processing option causes execution to return to the processing of biological samples. The Reporting option allows the user to process reporting data as shown in FIG. 11, and discussed below. Selecting the Other option allows the user to perform administrative tasks such as adding and/or removing users, and editing the default settings. This functionality is shown in FIG. 12 and is further discussed below.

FIG. 5 illustrates the functionality for plate set-up and assigning the plate number. The plate number may be read from the plate via a reader for a machine readable indicator, reading a barcode number as a non-limiting example, or entered manually by the user, via keyboard as a non-limiting example. After the plate number has been received by the system, the plate is placed on the machine. The system then obtains a work-list of batches that are ready to be processed, and these batches are moved to the plate as necessary for processing. The work-list is organized according to Laboratory Information Management Software (LIMS) plate number, number of samples, and list of samples.

Figure 6:
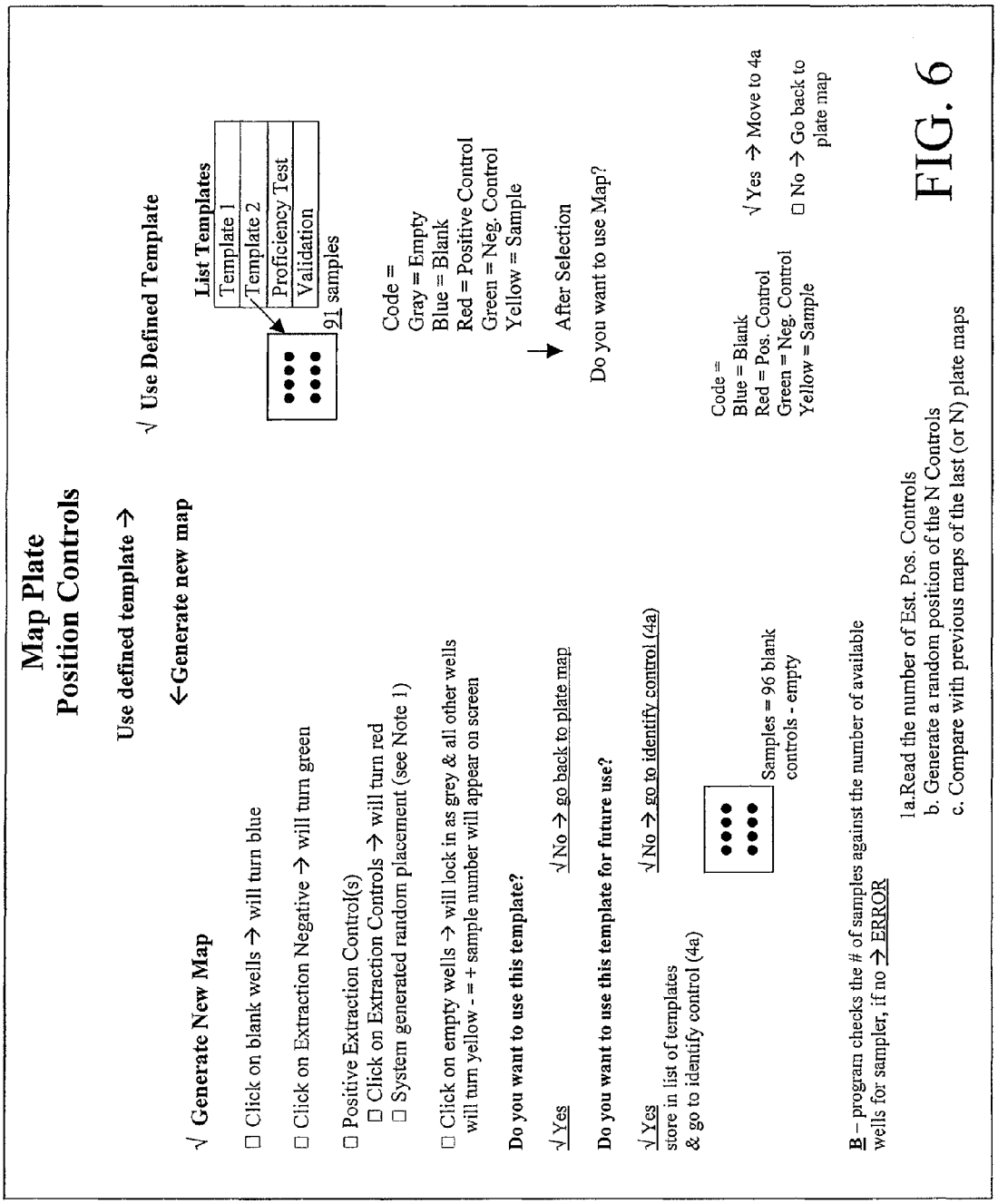
FIG. 6 is a diagram depicting the map plate position controls according to an embodiment of the present invention.

FIG. 6 illustrates the functionality for the Map Plate Position Controls. The user may use a defined template or generate a new map. After generating a new map, the user has the option of saving the template for future use. Defined templates, including previously generated maps, appear in the list of templates from which the user may select a template. In either case, the user has the option whether to use the selected or generated template; if the user does not wish to use the selected or generated template, the option to go back to the map plate position controls and begin again is presented.

The code for defined templates is gray for empty wells, blue for blank wells, red for positive control, green for negative control, and yellow for the sample. The color code can be modified. After selecting a defined template, the user is prompted whether to use the selected map.

The user may generate a new map as is also shown in FIG. 6. In the preferred embodiment, the map plate is a 96 well tray containing 12 columns and 8 rows and is displayed as a 12×8 matrix showing the well locations. The map plate display shows where certain samples should reside in the plate. Selecting blank wells causes them to turn blue. Selecting Extraction Negative will turn the wells green. For Positive Extraction Control(s), the user may select Extraction Controls to turn the wells red or the user may select system generated random placement. Selecting empty wells locks the wells as gray and the other wells become yellow.

If the user desires to use the selected or generated template, then functionality proceeds according to FIG. 7. Controls are identified based on the plate map. After the controls are entered, the user is queried as to whether the controls are correct. If the controls are not correct this process is performed again.

Figure 8:
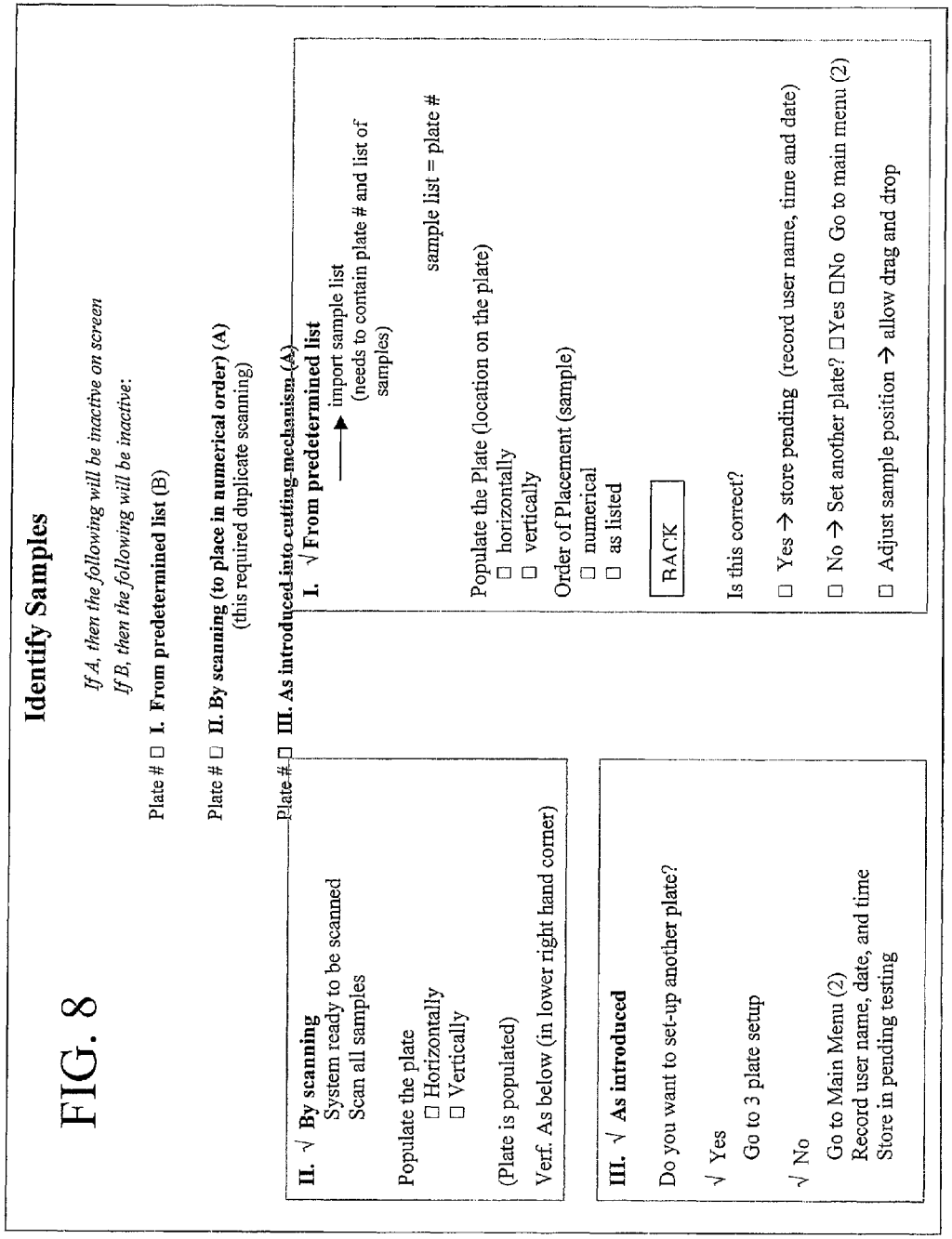
FIG. 8 is a diagram depicting the identify samples functionality according to an embodiment of the present invention.

If the controls are correct, functionality proceeds to identify the samples, as illustrated in FIG. 8. The plate may be populated according to a predetermined list, in numerical order (via scanning), or as introduced by the user. When identifying samples from a predetermined list, a sample list is imported. The sample list contains the plate number and the list of samples. Each sample is associated with a plate number. The plate is populated either horizontally or vertically. Further, the samples are populated either in numerical order or in the order listed in the sample list.

When identifying samples by scanning, the samples are scanned and the plate map is generated again, and the plate can be populated either horizontally or vertically. When identifying samples as introduced by the user, the user sets up the plate manually as in the plate set-up procedure discussed above however the plate map is not complete until all samples have been scanned and cut.

FIG. 9 illustrates the Position Plate functionality. The LIMS maintains a list of batches (plates) that are ready to be processed. If the batch is a pending file, then it has been set-up, but has not yet been processed. A Processing File is a batch that is in process. Once the processing is completed, the batch is moved to a Completed File. Each plate has a comment section associated with the plate ID number. A log file logs every action with a user name, date, and time. The plate number is either scanned or entered by the user, and then the plate(s) is placed on the X-Y positioning table. The number should correspond to a pending or processing plate(s). If the plate is not in the proper position, then the plate number will remain in the pending file and is re-entered or re-scanned. If the plate is in the proper position, then the plate number is moved from pending file to the processing file and functionality proceeds to Sample Processing. Camera pictures may also be captured by the system and saved under the plate number and comments.

Figure 10:
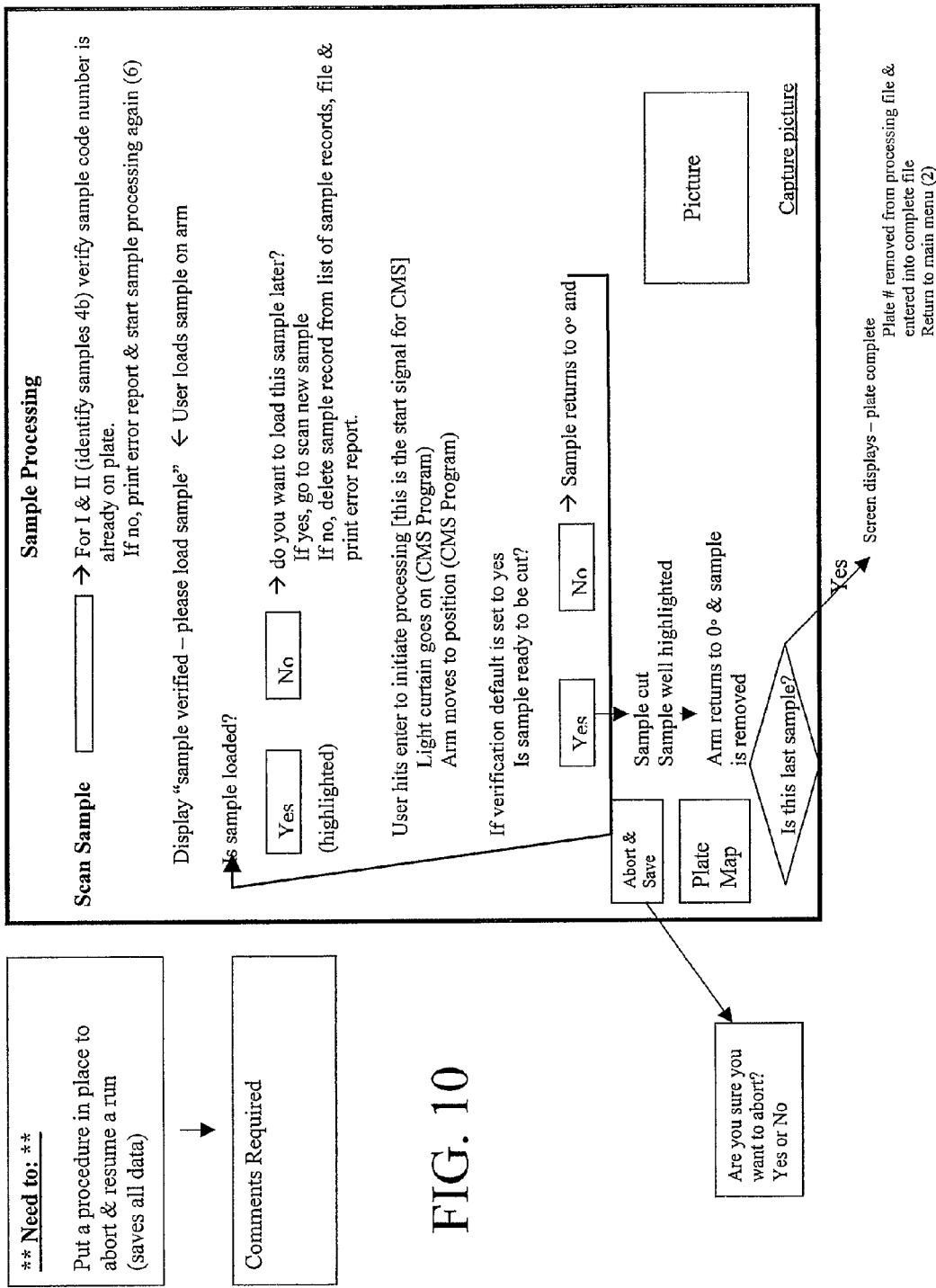
FIG. 10 is a diagram depicting sample processing functionality according to an embodiment of the present invention.

Sample Processing is illustrated in FIG. 10. Once a sample is scanned, the system will verify the sample code number is already on the plate. If the sample code number does not match the plate, then an error report is printed or displayed, and the sample processing begins again. Once verified, a message prompts the user to load the sample. The system prompts the user as to whether the sample has been loaded, and if the user responds affirmatively, then sample processing is initiated. If the user indicates that a sample is not loaded, then a message prompts the user whether to load this sample later. The user then may proceed by scanning a new sample. The user may also elect to delete the sample record from the list of sample records, after which an error report is filed and then printed/displayed.

After processing has been initiated, then the sample is moved into position. The user is prompted as to whether the sample is ready to be cut. If the user responds affirmatively, then the sample is cut and the user is queried as to whether this is the final cut. If this is the final cut, then a message is displayed indicating that the plate is complete, the plate number is removed from the processing file, and is entered into the complete file. Processing then returns to the main menu.

In the event that an abort is necessary, data is saved. After data has been saved from an abort operation, a run may be restarted.

Reports may be created as shown in FIG. 11, and may be printed or exported electronically. Comments and/or pictures associated with a plate number may be printed or exported. The plate number may be entered or selected from a menu. The user may elect to print or export a log file. Again, the log file may be entered or selected from a menu. The user may also print or export any pending plate numbers. An option also exists for exporting reports that have not previously been exported. Additionally, the user may record plate specific comments into the comments section for each plate.

The default parameters may be edited as shown in FIG. 12. The plate set-up option allows the plate number to be scanned from the plate or obtained from a work-list. The map plate may be processed according to a defined template or the user may generate a new template. Samples may be identified according to a predetermined list, scanning, or as introduced into the cutting mechanism. When identifying samples according to a predetermined list, the plate may be populated either horizontally or vertically, and the order of placement may be numerical or according to a list. For identifying samples by scanning, the plate may be populated either horizontally or vertically. An option also exists for whether the user desires to be asked to verify the sample position prior to cutting. Finally, an option can be set for the number of control placements to avoid in order to automatically "fingerprint" or code a plate using control samples to ensure the uniqueness of each plate and to detect inadvertent plate switches later in testing.

Figure 13:
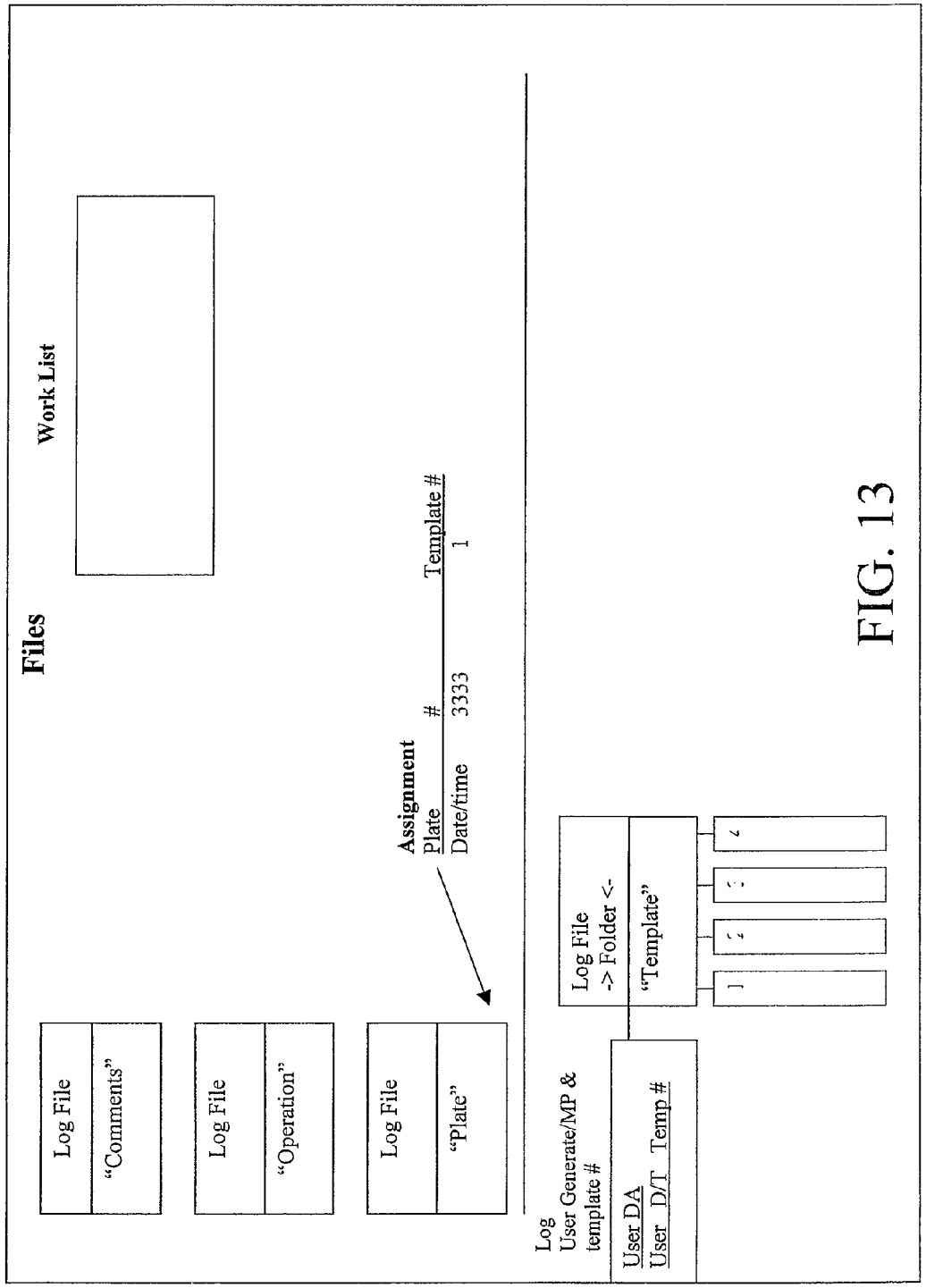
FIG. 13 is a diagram depicting the files functionality according to an embodiment of the present invention.

File management operates as shown in FIG. 13. During operation, the system creates log files that report events as they occur. There are three log files for comments, operation, and plate. The plate log file records the assignments of the plate number, the template number for that plate number, the date, and the time. Any user-entered comments are entered in the comments log file. The operation log file records any events that occur during processing. Examples of operation entries would be an electricity failure or user interruption and then the system is subsequently restarted after some period of time. Of course, operations that occur as expected could also be recorded. A work-list file is also maintained. The work-list is created by a user and contains templates to be operated upon by the system.

Figure 14:
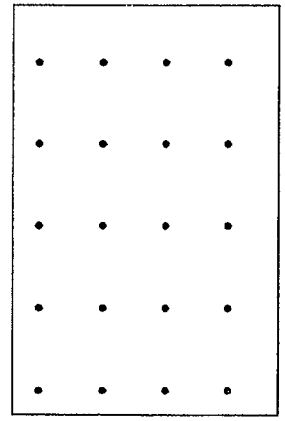
FIG. 14 is a diagram depicting the template functionality according to an embodiment of the present invention.

FIG. 14 shows the functionality assigning wells in the map plate. In the preferred embodiment, the map plate is a 96 well tray containing 12 columns and 8 rows. The map plate shows where certain samples should reside in the plate. Most holes are filled with actual samples. For some of the holes, the user may assign positive control, negative control, empty, or other. Each plate map is associated with a plate number and resides in the system memory. If an existing plate number is entered or retrieved by the user, then the system prompts that the number already exists. The user is then given an option whether to overwrite the template.

The contents of a well plate are shown in FIG. 15. Selecting Nothing indicates that a template will be specified by the user. Extraction Positive Controls (for known samples) will typically have 0-3 controls on a plate. The specific location may be generated by software (fingerprint plate) or specified by the user (user inputs a control number). Extraction Negative Control (blank) will be specified by the user to create a template. Samples may be processed from a predefined list (number on software, verification), introduced by the user, or introduced by the user and placed in numerical order.

Required information is shown in FIG. 16. The plate number is preferably unique with no duplicates allowed. The user is identified as well as the date and time. The samples are on the plate as well as controls. Comments are supplied for each plate. The LIMS is updated.

FIG. 17 illustrates features of the plate map. Samples and controls are color coded. A fingerprint plate provides a map for sample location. Samples may be sorted and arranged. Errors may be printed, saved, and sent to the LIMS.

FIG. 18 illustrates plate set-up. Plate numbers may be assigned automatically based on information from the LIMS, scanned in, or manually entered via the keyboard. Controls may be defined by template, computer driven, or both. Samples may be assigned electronically from the LIMS, scanned, or manually entered via the keyboard. Finally, the LIMS is updated.

It should be emphasized that the above-described embodiments, particularly, any "preferred" embodiments, are merely possible examples of implementations, merely set forth for a clear understanding of the principles of the automation of biological sample aliquoting processing system. Many variations and modifications may be made to the above-described embodiments of the automation of biological sample aliquoting processing system without departing substantially from the principles thereof. All such modifications and variations are intended to be included herein within the scope of this disclosure.

In addition to the foregoing, some example embodiments of the present invention are specifically outlined below as follows:

A. An automated biological sample processing system comprising:
  a reader for reading a machine readable indicator;
  a positioning table for positioning a multi-well plate;
  a cutting unit for cutting a biological collection device having a biological sample; and
  control software for causing a part of the biological collection device containing at least a part of the biological sample to be directed into a well within the multi-well plate.

B. The system as described in any one of the previous embodiments, and further comprising a data management system that maintains identification number(s) of at least one multi-well plate(s), at least one biological sample identification number corresponding to one of the at least one multi-well plate(s), and well location of the at least one biological sample identification number within the at least one multi-well plate(s).

C. The system as described in any one of the previous embodiments wherein the reader comprises a bar code reader.

D. The system as described in any one of the previous embodiments, wherein the cutting unit utilizes a non-contact technique.

E. The system as described in any one of the previous embodiments, wherein the cutting unit comprises a laser cutter.

F. The system as described in any one of the previous embodiments, wherein the cutting unit comprises a high-speed water jet.

G. The system as described in any one of the previous embodiments, wherein the biological collection device is a swab.

H. The system as described in any one of the previous embodiments, wherein the biological collection device is a paper collection device.

I. The system as described in any one of the previous embodiments, wherein the biological collection device is a sponge collection device.

J. The system as described in any one of the previous embodiments, wherein the biological collection device is a cloth collection device.

K. The system as described in any one of the previous embodiments, wherein the biological collection device is a plastic collection device.

L. The system as described in any one of the previous embodiments, wherein the biological collection device is a polymer collection device.

M. The system as described in any one of the previous embodiments, further comprising an optical sensor for adjusting the height of the biological collection device to an appropriate cut position.

N. The system as described in any one of the previous embodiments, further comprising a sample loading system for loading the biological collection device.

O. The system as described in any one of the previous embodiments, wherein the sample loading system is an automated robotic sample loading system.

P. The system as described in any one of the previous embodiments, wherein the sample loading system is an automated pneumatic sample loading system.

Q. The system as described in any one of the previous embodiments, wherein the sample loading system is an automated magnetic sample loading system.

R. The system as described in any one of the previous embodiments, wherein the sample loading system is a manual sample loading system.

S. An automated biological sample processing system for handling biological samples, comprising:

means for securing a biological collection device having a biological sample;

means for moving the biological collection device to a location over a well in a multi-well plate; and means for cutting the biological collection device to permit a part of the biological collection device containing at least a part of the biological sample to be directed into the well.

T. The system as described in embodiment R, wherein the biological collection device is a swab.

U. The system as described in any one of the previous embodiments set forth in embodiments R-S, wherein the biological collection device is a paper collection device.

V. The system as described in any one of the previous embodiments set forth in embodiments R-T, wherein the biological collection device is a sponge collection device.

W. The system as described in any one of the previous embodiments set forth in embodiments R-U, wherein the biological collection device is a plastic collection device.

X. The system as described in any one of the previous embodiments set forth in embodiments R-V, wherein the biological collection device is polymer collection device.

Y. The system as described in any one of the previous embodiments set forth in embodiments R-W, further comprising means for reading a bar code indicator associated with the biological collection device.

Z. The system as described in any one of the previous embodiments set forth in embodiments R—X, further comprising means for reading a bar code indicator associated with the multi-well plate.

AA. The system as described in any one of the previous embodiments set forth in embodiments R-Z, wherein the cutting means utilizes a non-contact cutting technique.

BB. The system as described in any one of the previous embodiments set forth in embodiments R-Z, further comprising means for tracking the location of at least one biological sample within at least one multi-well plate.

CC. The system as described in any one of the previous embodiments set forth in embodiments R-Z, further comprising means for causing at least one biological sample to be located in a specific location within at least one multi-well plate.

DD. A method for an automated sample processing system for handling samples, the method comprising the steps of:

securing a collection device having a collection sample;

moving the collection device to a location over a well in a multi-well plate; and cutting the collection device to permit a part of the collection device containing at least a part of the collection sample to be directed into the well.

EE. The method as described in any one of the previous embodiments set forth in embodiment CC, further comprising that the securing step collection sample comprises a biological sample.

FF. The method as described in any one of the previous embodiments set forth in embodiments CC-DD, further comprising the step of associating the collection sample with a sample identifier.

GG. The method as described in any one of the previous embodiments set forth in embodiments CC-EE, further comprising the step of associating the multi-well plate with a plate identifier.

HH. The method as described in any one of the previous embodiments set forth in embodiments CC-FF, further comprising the step of associating at least one sample identifier with the plate identifier.

II. The method as described in any one of the previous embodiments set forth in embodiments CC-GG, wherein the cutting step utilizes a non-contact cutting technique.

JJ. The method as described in any one of the previous embodiments set forth in embodiments CC-HH, wherein the cutting step utilizes a laser cutting technique.

KK. The method as described in any one of the previous embodiments set forth in embodiments CC-II, wherein the cutting step utilizes a high-speed water jet cutting technique.

LL. The method as described in any one of the previous embodiments set forth in embodiments CC-JJ, further comprising the step of verifying that the collection device is loaded prior to the cutting step.

MM. The method as described in any one of the previous embodiments set forth in embodiments CC-KK, further comprising the step of verifying that the collection device is ready to be cut prior to the cutting step.

NN. The method as described in any one of the previous embodiments set forth in embodiments CC or EE-LL, further comprising that the securing step collection sample comprises a buccal swab.

OO. The method as described in any one of the previous embodiments set forth in embodiments CC or EE-LL, further comprising that the securing step collection sample comprises a blood sample.

PP. The method as described in any one of the previous embodiments set forth in embodiments CC or EE-LL, further comprising that the securing step collection sample comprises a saliva sample.

QQ. The method as described in any one of the previous embodiments set forth in embodiments CC or EE-LL, further comprising that the securing step collection sample comprises a urine sample.

RR. The method as described in any one of the previous embodiments set forth in embodiments CC or EE-LL, further comprising that the securing step collection sample comprises a feces sample.

SS. The method as described in any one of the previous embodiments set forth in embodiments CC or EE-LL, further comprising that the securing step collection sample comprises a microbial sample.

TT. The method as described in any one of the previous embodiments set forth in embodiments CC or EE-LL, further comprising that the securing step collection sample comprises a pathogens sample.

UU. The method as described in any one of the previous embodiments set forth in embodiments CC or EE-LL, further comprising that the securing step collection sample comprises a forensic biological sample.

VV. The method as described in any one of the previous embodiments set forth in embodiments CC or EE-LL, further comprising that the securing step collection sample comprises a crime scene biological sample.

WW. The method as described in any one of the previous embodiments set forth in embodiments CC or EE-LL, further comprising that the securing step collection sample comprises a security issue related sample.

XX. The method as described in any one of the previous embodiments set forth in embodiments CC or EE-LL, further comprising that the securing step collection sample comprises a terrorist attack related sample.

YY. The method as described in any one of the previous embodiments set forth in embodiments CC or EE-LL, further comprising that the securing step collection sample comprises a microbial genetics sample.

ZZ. The method as described in any one of the previous embodiments set forth in embodiments CC or EE-LL, further comprising that the securing step collection sample comprises a forensic genetics sample.

AAA. The method as described in any one of the previous embodiments set forth in embodiments CC or EE-LL, further comprising that the securing step collection sample comprises a disease diagnostics sample.

BBB. The method as described in any one of the previous embodiments set forth in embodiments CC or EE-LL, further comprising that the securing step collection sample comprises a medical screening sample.

CCC. The method as described in any one of the previous embodiments set forth in embodiments CC or EE-LL, further comprising that the securing step collection sample comprises an identification sample.

DDD. The method as described in any one of the previous embodiments set forth in embodiments CC or EE-LL, further comprising that the securing step collection sample comprises a drug use sample.

EEE. The method as described in any one of the previous embodiments set forth in embodiments CC or EE-LL, further comprising that the securing step collection sample comprises an alcohol use sample.

FFF. The method as described in any one of the previous embodiments set forth in embodiments CC or EE-LL, further comprising that the securing step collection sample comprises a chemical use sample.

Therefore, having thus described the disclosure, at least the following is claimed:

1. An automated biological sample processing system comprising:
   a positioning table for positioning a multi-well plate;
   a cutting unit that utilizes a non-contact technique for cutting a biological collection device having a biological sample;
   an optical sensor employed in adjusting a height of the biological collection device; and
   a control system for causing a part of the biological collection device containing at least a part of the biological sample to be directed into a well within the multi-well plate.

2. The system of claim 1, further comprising a data management system that maintains at least one identification number of at least one multi-well plate, at least one biological sample identification number corresponding to one of the multi-well plate, and at least one well location associated with the at least one biological sample identification number within the at least one multi-well plate.

3. The system of claim 1, further comprising a reader for reading a machine readable indicator, wherein the reader comprises a bar code reader.

4. The system of claim 1, wherein the cutting unit comprises a laser cutter.

5. The system of claim 1, wherein the biological collection device is selected from a group consisting of a swab, a paper collection device, a sponge collection device, a cloth collection device, a plastic collection device, and a polymer collection device.

6. The system of claim 1, further comprising a sample loading system for loading the biological collection device.

7. The system of claim 6, wherein the sample loading system is selected from a group consisting of an automated robotic sample loading system, an automated pneumatic sample loading system, an automated magnetic sample loading system, a manual sample loading system.

8. An automated biological sample processing system comprising:
   a positioning table for positioning a target vessel;
   a cutting unit that utilizes a non-contact technique for cutting a biological collection device having a biological sample;
   an optical sensor employed in adjusting a height of the biological collection device; and
   a control system for causing a part of the biological collection device containing at least a part of the biological sample to be directed into a well within the target vessel.

9. The system of claim 8, further comprising a data management system that maintains at least one identification number of the target vessel, at least one biological sample identification number corresponding to the target vessel, and at least a well location associated with the at least one biological sample identification number within the target vessel.

10. The system of claim 9, wherein the data management system further maintains a well location associated with the at least one biological sample identification number within the target vessel.

11. The system of claim 8, further comprising a reader for reading a machine readable indicator, wherein the reader comprises a bar code reader.

12. The system of claim 8, wherein the cutting unit comprises a laser cutter.

13. The system of claim 8, wherein the biological collection device is selected from a group consisting of a swab, a paper collection device, a sponge collection device, a cloth collection device, a plastic collection device, and a polymer collection device.

14. The system of claim 8, further comprising a sample loading system for loading the biological collection device.

15. The system of claim 14, wherein the sample loading system is selected from a group consisting of an automated robotic sample loading system, an automated pneumatic sample loading system, an automated magnetic sample loading system, a manual sample loading system.

* * * * *

UNITED STATES PATENT AND TRADEMARK OFFICE
CERTIFICATE OF CORRECTION

PATENT NO. : 7,745,204 B1  
APPLICATION NO. : 11/380239  
DATED : June 29, 2010  
INVENTOR(S) : Cyrus K. Aidun et al.

Page 1 of 1

It is certified that error appears in the above-identified patent and that said Letters Patent is hereby corrected as shown below:

At column 12, line 11, delete "embodiment CC," and replace with --embodiment DD,--.

At column 12, line 15, delete "embodiments CC-DD," and replace with --embodiments DD-EE,--.

At column 12, line 19, delete "embodiments CC-EE," and replace with --embodiments DD-FF,--.

At column 12, line 19, delete "embodiments CC-FF," and replace with --embodiments DD-GG,--.

At column 12, line 27, delete "embodiments CC-GG," and replace with --embodiments DD-HH,--.

At column 12, line 31, delete "embodiments CC-HH," and replace with --embodiments DD-II,--.

At column 12, line 35, delete "embodiments CC-II," and replace with --embodiments DD-JJ,--.

At column 12, line 39, delete "embodiments CC-JJ," and replace with --embodiments DD-KK,--.

At column 12, line 43, delete "embodiments CC-KK," and replace with --embodiments DD-LL,--.

At column 12, lines 47, 51, 55, 59, 63, 67 and column 13, lines 4, 8, 12, 16, 20, 23, 27, 31, 35, 39, 42, 46, 50, delete "embodiments CC or EE-LL," and replace with --embodiments DD or FF-MM,--.

Signed and Sealed this  
Twenty-eighth Day of December, 2010

David J. Kappos  
*Director of the United States Patent and Trademark Office*